United States Patent
Hapola et al.

(10) Patent No.: US 11,743,687 B2
(45) Date of Patent: *Aug. 29, 2023

(54) METHOD AND SYSTEM FOR DETERMINING AND TRACKING AN INDOOR POSITION OF AN OBJECT

(71) Applicant: Suunto Oy, Vantaa (FI)

(72) Inventors: Tuomas Hapola, Vantaa (FI); Heikki Nieminen, Vantaa (FI); Mikko Martikka, Vantaa (FI); Erik Lindman, Vantaa (FI)

(73) Assignee: Suunto Oy, Vantaa (FI)

( * ) Notice: Subject to any disclaimer, the term of this patent is extended or adjusted under 35 U.S.C. 154(b) by 0 days.

This patent is subject to a terminal disclaimer.

(21) Appl. No.: 17/224,246

(22) Filed: Apr. 7, 2021

(65) Prior Publication Data

US 2021/0258733 A1 Aug. 19, 2021

Related U.S. Application Data

(63) Continuation of application No. 16/884,118, filed on May 27, 2020, now Pat. No. 10,999,709, which is a
(Continued)

(30) Foreign Application Priority Data

Oct. 31, 2017 (FI) ..................................... 20175966
Oct. 31, 2017 (GB) ..................................... 1717965

(51) Int. Cl.
*G01C 21/16* (2006.01)
*G01C 21/20* (2006.01)
(Continued)

(52) U.S. Cl.
CPC ......... *H04W 4/029* (2018.02); *A63B 24/0021* (2013.01); *G01C 17/28* (2013.01);
(Continued)

(58) Field of Classification Search
CPC .. H04W 4/029; H04W 4/026; A63B 24/0021; A63B 2024/0025; A63B 2220/40;
(Continued)

(56) References Cited

U.S. PATENT DOCUMENTS 6,122,960 A 9/2000 Hutchings et al.
6,813,582 B2 11/2004 Levi et al.
(Continued)

FOREIGN PATENT DOCUMENTS

CN 101661048 A 3/2010
CN 103154954 A 6/2013
(Continued)

OTHER PUBLICATIONS

Jardak et al: Detection and localization of multiple short range targets using FMCW radar signal. Global Symposium on Millimeter Waves & ESA Workshop on Millimetre-Wave Technology and Applicaitons, 2016.

*Primary Examiner* — Joseph E Dean, Jr.
(74) *Attorney, Agent, or Firm* — Laine IP Oy

(57) ABSTRACT

According to an example aspect of the present invention, there is provided a method and system for determining and tracking an indoor position of an object, the method comprising: using a primary position indication, based on signals received from an external positioning system of at least two different positions of said object to calibrate tracking of a secondary position indication, which is an indoor position, and wherein the tracking of the secondary position comprises: recording acceleration data of a second part of the object, integrating said acceleration data, determining a characteristic position of the cyclically moving second part of the object in subsequent cycles, measuring a geomagnetic first orientation of the second part of the object in said characteristic position, determining the second direction of movement of the first part of the object, computing a
(Continued)

velocity of the object in any direction based on the acceleration data, and determining the secondary position indication of said object based on said direction data and said velocity data.

26 Claims, 10 Drawing Sheets

Related U.S. Application Data continuation of application No. 16/693,416, filed on Nov. 25, 2019, now Pat. No. 10,708,723, which is a continuation of application No. 16/168,953, filed on Oct. 24, 2018, now Pat. No. 10,555,127.

(51) Int. Cl.
| | | |
|---|---|---|
| *H04W 4/029* | (2018.01) | |
| *G16H 20/30* | (2018.01) | |
| *G07C 1/22* | (2006.01) | |
| *H04W 4/02* | (2018.01) | |
| *A63B 24/00* | (2006.01) | |
| *G01C 17/28* | (2006.01) | |
| *G01C 21/08* | (2006.01) | |
| *G01C 21/18* | (2006.01) | |

(52) U.S. Cl.
CPC ......... *G01C 21/08* (2013.01); *G01C 21/1654* (2020.08); *G01C 21/18* (2013.01); *G07C 1/22* (2013.01); *G16H 20/30* (2018.01); *H04W 4/026* (2013.01); *A63B 2024/0025* (2013.01); *A63B 2220/40* (2013.01)

(58) Field of Classification Search
CPC ........ G01C 17/28; G01C 21/08; G01C 21/18; G01C 21/165; G01C 21/206; G07C 1/22; G16H 20/30

See application file for complete search history.

(56) References Cited

U.S. PATENT DOCUMENTS

| | | |
|---|---|---|
| 10,595,143 B2 | 3/2020 | Norris et al. |
| 10,708,723 B2 | 7/2020 | Hapola |
| 2003/0191582 A1 | 10/2003 | Terada |
| 2004/0192269 A1 | 9/2004 | Hill |
| 2006/0247847 A1 | 11/2006 | Carter |
| 2009/0254276 A1 | 10/2009 | Faulkner et al. |
| 2011/0208444 A1 | 8/2011 | Solinsky |
| 2012/0062414 A1* | 3/2012 | Sambongi .......... G01C 21/1656 342/357.25 |
| 2014/0200847 A1 | 7/2014 | Singiresu et al. |
| 2014/0320674 A1 | 10/2014 | Kuang |
| 2015/0134294 A1* | 5/2015 | Mizuochi ............. A61B 5/7235 702/151 |
| 2015/0142312 A1 | 5/2015 | Shin et al. |
| 2015/0198462 A1 | 7/2015 | Hsieh |
| 2017/0011210 A1 | 1/2017 | Cheong et al. |
| 2017/0059327 A1* | 3/2017 | Miller ................. G01C 21/165 |

FOREIGN PATENT DOCUMENTS

| | | |
|---|---|---|
| CN | 103502773 A | 1/2014 |
| CN | 105102928 A | 11/2015 |
| CN | 105934655 A | 9/2016 |
| CN | 106679649 A | 5/2017 |
| GB | 2497153 A | 6/2013 |
| TW | 486576 A | 5/2002 |
| TW | 201107780 A | 3/2011 |
| WO | WO0036520 A1 | 6/2000 |
| WO | WO2014110672 A1 | 7/2014 |
| WO | WO2014113874 A1 | 7/2014 |

* cited by examiner

METHOD AND SYSTEM FOR DETERMINING AND TRACKING AN INDOOR POSITION OF AN OBJECT

FIELD

The present invention relates to a method for determining and tracking an indoor position of an object.

Further, the present invention relates to a system for determining and tracking an indoor position of an object.

Furthermore, the present invention relates to a non-transitory computer readable medium.

In particular, embodiments of the present invention relate to sensor technology in mobile devices, i.e. more specifically to processing of information provided by a multitude of sensors. The invention particularly relates to improving the accuracy of a position indication measured with the aid of a mobile device or system. The mobile device may be, for example, a wristop computer, a mobile telephone or any other portable device.

BACKGROUND

The signal from a GPS (Global Positioning System) sensor or other satellite-based navigation system located in a device carried by a person on the wrist or elsewhere on the body, has a very small bias error, i.e. a systematic error, but contains a great deal of noise. At a measurement frequency of 1 Hz with the person walking or running, the noise in a purely GPS-based speed measurement can be in the order of 20-30%, compared to the pure GPS signal.

Direction or speed data measured and estimated from sensors carried directly on the body of a person, contains usually less noise. However, large bias errors may be present in these measurement signals.

Sensor fusion means that first and second sensors may be based on different operating principles, but they are measuring the same physical variable. For example, horizontal speed can be measured using a satellite-positioning sensor or an acceleration sensor. Sensors that can be used in sensor fusion may be, for example, a GPS sensor, a magnetometer (compass), and acceleration sensors. With such sensors, the acceleration, speed and direction of a moving object may be measured and displayed on a mobile device, for example on the display of a wristop computer, a mobile telephone or any other portable device.

It is known from GB 2497153 to measure first and second physical variables with first and second sensors respectively, and to determine an estimate of a target variable by measuring a first physical variable. An error estimate is determined by measuring a second physical variable, and the estimate of the target variable is filtered with a strength that depends on the error estimate. However, during a loss of satellite signals, as may be the case in shadow areas such as in tunnels, backyards and mountain areas, where only a weak or non-detectable positioning signal strength exists, a satellite-based measurement may not be available at all.

Therefore, there is a need for a method and system capable of determining the direction of movement of an object. The method and system should be, for example, usable for a positioning system that delivers accurate and uninterrupted position data and other data derivable therefrom. In view of the foregoing, it would be beneficial to provide a method and a system capable of determining the direction of movement of an object comprising a first part and a second part which is cyclically moving relative to the first part, in which method and system the battery consumption can be reduced. It would be also beneficial to provide a method and system capable of providing uninterrupted position data and other data derivable therefrom.

SUMMARY OF THE INVENTION

The invention is defined by the features of the independent claims. Some specific embodiments are defined in the dependent claims.

Certain embodiments of the present invention provide a new type of method and system for determining direction of movement of an object as well as positioning and navigation services in a mobile device, and a corresponding system. The object of certain embodiments of the invention is particularly to complement GPS positioning services, or any other positioning service, for example wireless positioning services, visual location services, or a location given by a user, with position information derived from other sensors, in varying movement and ambient conditions.

According to a first aspect of the present invention, there is provided a method for determining a direction of movement of an object, the method comprising determining a cyclical motion of a cyclically moving part of the object by recording acceleration data of said cyclically moving part over a plurality of cycles using an accelerometer or inertial sensor attached to said cyclically moving part, integrating said acceleration data over at least one cycle of movement to determine a tilting of said cyclically moving part of the object, determining a characteristic position of the cyclically moving part in subsequent cycles, measuring an external magnetic field of said cyclically moving part of the object using a magnetometer to determine an orientation of said cyclically moving part of the object relative to the external magnetic field, determining the direction of movement of the object based on the tilting and the orientation of said cyclically moving part of the object.

Various embodiments of the first aspect may comprise at least one feature from the following bulleted list:

- a characteristic position of the cyclically moving part is determined in subsequent cycles
- the external magnetic field of said cyclically moving part is measured in said characteristic position
- the direction of movement of the object is determined based on a previously determined direction of said object and the orientation of the cyclically moving part of the object
- the direction of movement of the object is determined based on a previously determined direction of said object and a measured geomagnetic orientation of the cyclically moving part of the object
- the previously determined direction of said moving object is determined based on signals received from an external positioning system
- the previously determined direction of said moving object is determined based on GPS signals measured at two separate points of time
- a first direction of a moving first part of the object is determined based on signals received from an external positioning system, acceleration data of a second part of the object is recorded, which second part is cyclically moving relative to the first part of the object, over a plurality of cycles using an accelerometer or inertial sensor attached to the second part of the object, said acceleration data is integrated over at least one cycle of movement to determine the tilting of said cyclically moving part of the object relative to the horizontal plane, a characteristic position of the cyclically moving second part of the object is determined in subsequent cycles, a geomagnetic first orientation of the second part of the object is measured in said characteristic position using a magnetometer, a second direction of movement of the first part of the object is determined by measuring a geomagnetic second orientation of the second part of the object in said characteristic position using a magnetometer, and wherein the determination is based on the tilting and the deviation between the geomagnetic first orientation and the geomagnetic second orientation of the second part of the object at least one of the first direction, the second direction, an acceleration, a velocity, and a position of the first part of the moving object is tracked at least one of a first angle between the geomagnetic first orientation of the second part of the object and the first direction of the first part of the object and a second angle between the geomagnetic first orientation and the geomagnetic second orientation of the second part of the object is determined a third angle between the geomagnetic second orientation of the second part of the object and the second direction of the first part of the object is identical with the first angle a position of the first part of the object is determined with the combined use of the external positioning system to determine the first direction of the first part of the object, the accelerometer or inertial sensor to determine the acceleration data, the magnetometer to determine the first orientation and the second orientation of the second part of the object, and a timing function used to record the time the object has moved in any direction the time the object has moved in any direction is recorded by a timing function the tilting of the accelerometer or inertial sensor is determined using the formula $$\int_C \vec{a} = \int_C \vec{a} + \int_C f(\vec{g}) \approx \vec{0} + \vec{O} \cdot \Delta t,$$

wherein $\vec{a}$ is the acceleration of the second part, $\vec{g}$ is the gravity in global coordinates, $\vec{O}$ is the tilt, and t is the time air pressure is measured by means of an air pressure sensor and an altitude of said object is determined based on the air pressure a position of the moving object is displayed on a display of a system, transmitted from the system to another device, or shown on a map which is available via internet the position is an indoor or an outdoor position the position is determined in real time or at a later stage the characteristic position of each cycle is at a maximum or minimum acceleration value a track formed in a first coordinate system is aligned with a second coordinate system According to a second aspect of the present invention, there is provided a system for determining a direction of movement of an object, the system comprising a receiver for receiving signals from an external positioning system, at least one of an accelerometer or an inertial sensor, a magnetometer, at least one memory unit, and a processing unit comprising at least one processing core, at least one memory including computer program code, the at least one memory and the computer program code being configured to, with the at least one processing core, cause the system at least to determine a cyclical motion of a cyclically moving part of the object by recording acceleration data of said cyclically moving part over a plurality of cycles using an accelerometer or inertial sensor attached to said cyclically moving part, integrate said acceleration data over at least one cycle of movement to determine a tilting of said cyclically moving part of the object relative to a horizontal plane, measure an external magnetic field of said cyclically moving part of the object using a magnetometer to determine an orientation of said cyclically moving part of the object relative to the external magnetic field, determine the direction of movement of the object based on the tilting and the orientation of the cyclically moving part of the object.

Various embodiments of the second aspect may comprise at least one feature from the following bulleted list:

the system is configured to determine a characteristic position of the cyclically moving part in subsequent cycles the system is configured to measure the external magnetic field of the cyclically moving part in said characteristic position the system is configured to determine the direction of movement of the object based on a previously determined direction of said object and the orientation of the cyclically moving part of the object the system is configured to determine the direction of movement of the object based on a previously determined direction of said object and a measured geomagnetic orientation of the cyclically moving part of the object the system is configured to determine the previously determined direction of said moving object based on signals received from an external positioning system the system is configured to determine the previously determined direction of said moving object based on GPS signals measured at two separate points of time the processing unit comprising the at least one processing core, the at least one memory including computer program code, the at least one memory and the computer program code is further configured to, with the at least one processing core, cause the system at least to determine a first direction of a moving first part of the object based on signals received from an external positioning system, record acceleration data of a second part of the object, which second part is cyclically moving relative to the first part of the object, over a plurality of cycles using an accelerometer or inertial sensor attached to the second part of the object, integrate said acceleration data over at least one cycle of movement to determine a tilting of said cyclically moving part of the object relative to a horizontal plane, determine a characteristic position in subsequent cycles, measure an external magnetic field of the second part of the object in a characteristic position of subsequent cycles using a magnetometer, measure a geomagnetic second orientation of the second part of the object in the characteristic position of each cycle using the magnetometer, determine a second direction of the first part of the moving object based on the tilting and a deviation between the geomagnetic first orientation and the geomagnetic second orientation of the second part of the object the processing unit is continuously computing and storing at least one of the first direction, the second direction, an acceleration, a velocity, and a position of the first part of the moving object the system is configured to determine the first direction of the first part of the object based on GPS signals between two separate points of time the system is configured to track at least one of the first direction, the second direction, an acceleration, a velocity and a position of the first part of the moving object the system is configured to determine at least one of a first angle between the geomagnetic first orientation of the second part of the object and the first direction of the first part of the object and a second angle between the geomagnetic first orientation and the geomagnetic second orientation of the second part of the object the system is configured to determine a position of the first part of the object with the combined use of the external positioning system to determine the first direction of the first part of the object, the accelerometer or inertial sensor to determine the acceleration data, the magnetometer to determine the first orientation and the second orientation of the second part of the object, and a timing function used to record the time the object has moved in any direction the system is configured to record the time the object has moved in any direction by a timing function the system is configured to determine the tilting of the accelerometer or inertial sensor using the formula $$\int_C \vec{a} = \int_C \vec{a} + \int_C f(\vec{g}) \approx \vec{O} + \vec{O} \cdot \Delta t,$$

wherein $\vec{a}$ is the acceleration of the second part, $\vec{g}$ is the gravity in global coordinates, $\vec{O}$ is the tilt, and t is the time the system further comprises an air pressure sensor the system is configured to display a position of the moving object on a display of the system, to transmit the position of the moving object from the system to another device, or to show the position of the moving object on a map which is available via internet the system is configured to track an indoor or an outdoor position of the moving object the system is configured to determine the position in real time or at a later stage the system further comprises a gyroscope the system is configured to align a track formed in a first coordinate system with a second coordinate system According to a third aspect of the present invention, there is provided a non-transitory computer readable medium having stored thereon a set of computer readable instructions that, when executed by at least one processor, cause an apparatus to at least to determine a cyclical motion of a cyclically moving part of the object by recording acceleration data of said cyclically moving part over a plurality of cycles using an accelerometer or inertial sensor attached to said cyclically moving part, integrate said acceleration data over at least one cycle of movement to determine a tilting of said cyclically moving part of the object relative to a horizontal plane, measure an external magnetic field of said cyclically moving part of the object using a magnetometer to determine an orientation of said cyclically moving part of the object relative to the external magnetic field, determine the direction of movement of the object based on the tilting and the orientation of the cyclically moving part of the object.

Various embodiments of the third aspect may comprise at least one feature corresponding to a feature from the preceding bulleted list laid out in connection with the first aspect or second aspect.

Considerable advantages are obtained by certain embodiments of the invention. A method and a system for determining the direction of movement of an object are provided. It is possible to track the position of an object by means of the provided compass in the coordinate system the as described compass forms. The coordinate system can be aligned with any other coordinate system, for example one can even afterwards align the track to a geographical track.

According to a certain embodiment, an external positioning system is only required for calibration of a first direction into which the object is moving. Subsequently, the position of the object can be calculated based on deviations between different orientations of a second part of the object in characteristic positions during cyclical motions of the second part of the object. The calibration may only be carried out once or in certain time intervals, for example. Thus, battery consumption of the system in accordance with at least some embodiments of the present invention can be reduced, because the use of the external positioning system, for example a GPS positioning system, can be significantly reduced.

The object may be, for example, a rowing boat or a bicycle. The object may be also a human running, swimming, or rowing a boat, for instance. The position of any object can be determined as long as a second part of the object is cyclically moving relative to a first part of the object, the motion evolves very slowly compared to the time it takes to complete one cycle, and the horizontal velocity of the object's centre of mass is constant and the integral of vertical velocity is zero. Further, the invention particularly relates to improving the accuracy of a position indication measured with the aid of a mobile device or system. The mobile device may be, for example, a wristop computer, a mobile telephone or any other portable device.

Further, during loss of satellite signals, as may be e.g. the case in shadow areas such as in tunnels, in and between buildings, backyards, and mountain areas, where only a weak or non-detectable positioning signal strength exists and a satellite-based measurement is not possible, a positioning method and system that delivers accurate and uninterrupted position data and other data derivable therefrom, under all circumstances, is provided.

Direction data, velocity data, and position indication data and other data derivable therefrom may be provided in real time and/or at a later stage. The direction data, velocity data, and the position indication data and other data derivable therefrom may be visualized on a display of the system in accordance with at least some embodiments of the present invention, on another device, or in the internet.

The data may be e.g. used to calculate and/or monitor the covered distance or for safety reasons. A runner may want to know the covered distance during an exercise session in real time and/or at a later stage. Further, a person walking cross country may have the desire to know the real time location in case of an accident, for instance. In both cases, the method and system in accordance with at least some embodiments of the present invention can provide accurate and uninterrupted position data.

Further, an indoor position may be calculated by means of certain embodiments of the present invention. The position in a tunnel or in another building such as a sports stadium, where an external positioning signal is not available or the quality of the signal is not sufficient, may be calculated, for instance. The calculated position indication may be, for example, used in case of emergency. The calculated position indication may be, for example, transmitted to a server or by means of a smartphone app to an emergency doctor or other emergency forces, thus improving safety of a user.

EMBODIMENTS

Figure 1:
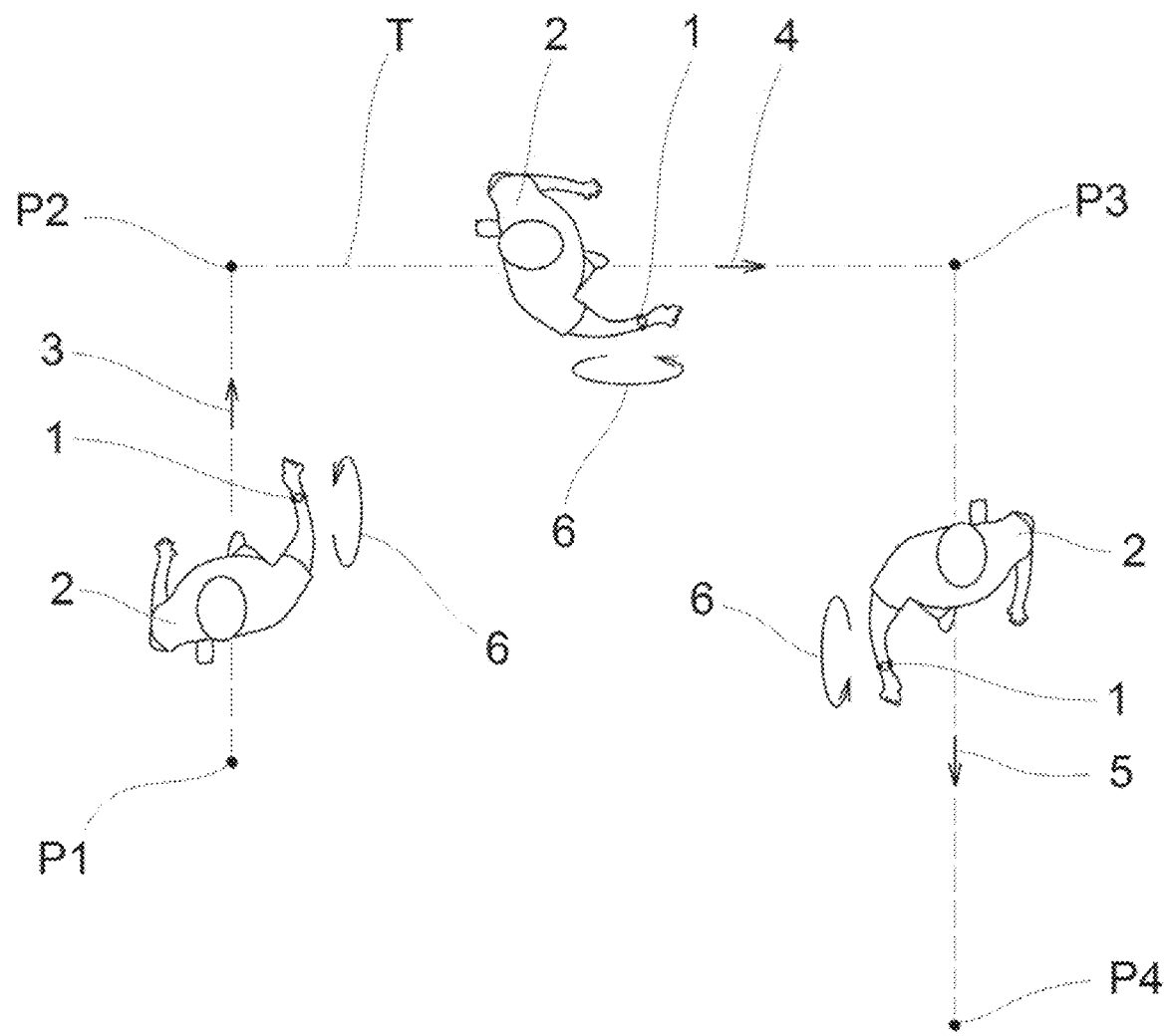
FIG. 1 illustrates a schematic view of an example of determination of a direction of movement of an object in accordance with at least some embodiments of the present invention.

In FIG. 1 a schematic view of an example of determination of a direction of movement of an object in accordance with at least some embodiments of the present invention is illustrated. A person 2 carrying a system 1 in accordance with certain embodiments of the present invention is about to run along a track T. The system 1 may be a wristop computer which is attached to the right arm of the person 2, for instance.

It is further relied on the observation that running is a cyclical motion. With cycle it is meant that a back and forth movement is made by an arm of a runner or a step pair. Throughout this document, the following assumptions are made:

1. A runner's running form evolves very slowly compared to the time it takes to complete one cycle, and
2. The horizontal velocity of the runner's centre of mass is constant and the integral of vertical velocity is zero.

These assumptions mean that the runner's wrist, or any other part of the body, is in the same orientation at the end of the cycle as at the beginning of the cycle.

In general, the forearm of a runner is not pointing to the direction of movement of the runner. When running, the arms of the person 2 move cyclically in relation to the body of the person 2. The cyclical motion 6 may be angular or linear, for example. In other words, a first part of the person 20 moves into a first direction 3 and a second part of the person 20 moves cyclically relative to the first part of the person 20. The term cyclically motion means that a motion is repeated in specific time intervals.

For reasons of calibration of the system 1, the first direction 3 of the first part of the person 2, i.e. the body of the person 2, is determined based on signals received from an external positioning system. For example, the first direction 3 of the first part of the person 2 is determined based on GPS signals between two separate points P1, P2. In the example shown in FIG. 1, the first direction 3 is orientated towards North.

Between the first point P1 and the second point P2 acceleration data of the second part of the person 2, i.e. at the position where the system 1 is attached to the arm of the person 2, is recorded over a plurality of cycles using an accelerometer or inertial sensor. The accelerometer or inertial sensor is attached to the second part of the person 2, i.e. to the right arm of the person 2. As the accelerometer or inertial sensor is comprised by the wristop computer, acceleration data is recorded at the position of the wristop computer. An accelerometer sampling frequency may be, for example, 104 Hz. In other words, the acceleration of the body, i.e. data from which a velocity and a position of the person 2 can be derived, and the acceleration of the arm to which the wristop computer is attached to are different due to the cyclical motion of the arms of the person 2.

A characteristic position can be determined in subsequent cycles of the cyclic motion. The characteristic position of each cycle may be at a maximum or minimum acceleration value, for example. One way to determine the cycles is to consider total acceleration and to count the peaks which correspond to the step. Then every second step, or a peak, completes a cycle. Also an adaptive peak finding algorithm may be used, for instance. An n-second sliding window is provided to calculate a mean and standard deviation. A maximum value is accepted after the signal drops below the mean minus a coefficient times standard deviation.

When integrating the acceleration data over the full cycles, the dynamic acceleration, i.e. the motion of the arm in relation to the body, integrates to zero. Only the gravity multiplied with the cycle duration for each axis respectively is left. In other words, an error caused by the acceleration of the arm relative to the body can be eliminated by integrating the acceleration data over the full cycles and an orientation of the accelerometer 13 or inertial sensor relative to a horizontal plane can be determined.

The orientation of the accelerometer 13 or inertial sensor relative to the horizontal plane, i.e. the tilting, can be determined or estimated in the characteristic position of each cycle. The tilt of the accelerometer can be e.g. determined or estimated using the formula $$\int_C \vec{a} = \int_C \vec{a} + \int_C f(\vec{g}) \approx \vec{O} + \vec{O} \cdot \Delta t,$$

wherein $\vec{a}$ is the acceleration of the second part of the person 2, $\vec{g}$ is the gravity in global coordinates, $\vec{O}$ is the tilt, and t is the time.

Additionally, an external magnetic field is measured using a magnetometer in order to determine orientation(s) of the cyclically moving part of the object 2 relative to the external magnetic field. For example, a geomagnetic first orientation of the second part of the person 2 in the characteristic position of each cycle, i.e. a heading, is determined using the magnetometer. The sampling frequency of the magnetometer may be, for example, 10 Hz. Subsequently, a first angle between the first orientation of the second part of the person 2 and the first direction 3 of the first part of the person can be determined.

Between the second point P2 and the third point P3 the person 2 is moving into a second direction 4. In the example shown in FIG. 1, the second direction 4 is orientated towards East. Acceleration data is recorded between points P1 and P2. Further, acceleration data is integrated over the full cycles to determine the tilting of the accelerometer 13 or inertial sensor relative to a horizontal plane. Furthermore, a characteristic position is determined in subsequent cycles. Additionally, a geomagnetic second orientation of the second part of the person 2 in the characteristic position of each cycle is determined using the magnetometer. The second direction 4 of the first part of the person 2 can now be determined based on the tilting and the deviation between the geomagnetic first orientation and the geomagnetic second orientation of the second part of the person. A second angle between the geomagnetic first orientation and the geomagnetic second orientation of the second part of the person 2 can be determined. A third angle between the geomagnetic second orientation of the second part of the person 2 and the second direction 4 of the first part of the person 2 is identical with the first angle, and thus the second direction 4 can be determined based on the deviation between the geomagnetic first orientation and the geomagnetic second orientation of the second part of the person 2. In other words, the deviation between the geomagnetic first orientation and the geomagnetic second orientation of the second part of the person 2 is identical with the deviation between the first direction 3 and the second direction 4 of the person 2.

Between the third point P3 and the fourth point P4 the person 2 is moving into a third direction 5. In the example shown in FIG. 1, the third direction 5 is orientated towards South. Acceleration data is recorded between points P3 and P4. Further, acceleration data is integrated over the full cycles to determine the tilting of the accelerometer 13 or inertial sensor relative to a horizontal plane. Furthermore, a characteristic position is determined. Additionally, a geomagnetic third orientation of the second part of the person 2 in the characteristic position of each cycle is determined using the magnetometer. The third direction 5 of the first part of the person 2 can now be determined based on the deviation between the geomagnetic second orientation and the geomagnetic third orientation of the second part of the person. A second angle between the geomagnetic second orientation and the geomagnetic third orientation of the second part of the person can be determined. A third angle between the geomagnetic third orientation of the second part of the person and the third direction 5 of the first part of the person is identical with the first angle, and thus the third direction 5 can be determined based on the tilting and the deviation between the geomagnetic second orientation and the geomagnetic third orientation of the second part of the person 2. In other words, the deviation between the geomagnetic second orientation and the geomagnetic third orientation of the second part of the person 2 is identical with the deviation between the second direction 4 and the third direction 5 of the person 2.

According to certain embodiments, each direction 3, 4, 5 and the velocity of the first part of the moving person 2 can be tracked, and thus a position of the person can be calculated. The position of the first part of the person 2 is determined with the combined use of different systems. An external positioning system is used to determine the first direction 3 of the first part of the person 2, i.e. for reasons of calibration. An accelerometer or inertial sensor is used to determine the acceleration data. A magnetometer is used to measure the geomagnetic first orientation, the geomagnetic second orientation, and any further geomagnetic orientation of the second part of the person 2. A timing function is further used to record the time the object has moved in any direction 3, 4, 5. A tracked position of the first part of the person 2 can be displayed on a display of the system, transmitted from the system to another device, or shown on a map which is available via internet. The tracked position may be an indoor or an outdoor position. The tracked position may be determined in real time or at a later stage.

Battery consumption of the system 1 in accordance with at least some embodiments of the present invention can be reduced, because the use of the external positioning system, for example a GPS positioning system, can be significantly reduced. According to certain embodiments, the external positioning system is used only for calibration of the system 1. According to certain embodiments, the external calibration system is used in certain time intervals, for example every 30 seconds or every 60 seconds. According to certain embodiments, the external positioning system is used to constantly calibrate the system 1. According to certain embodiments, the external positioning system is used when the signal strength exceeds a threshold value.

Figure 2:
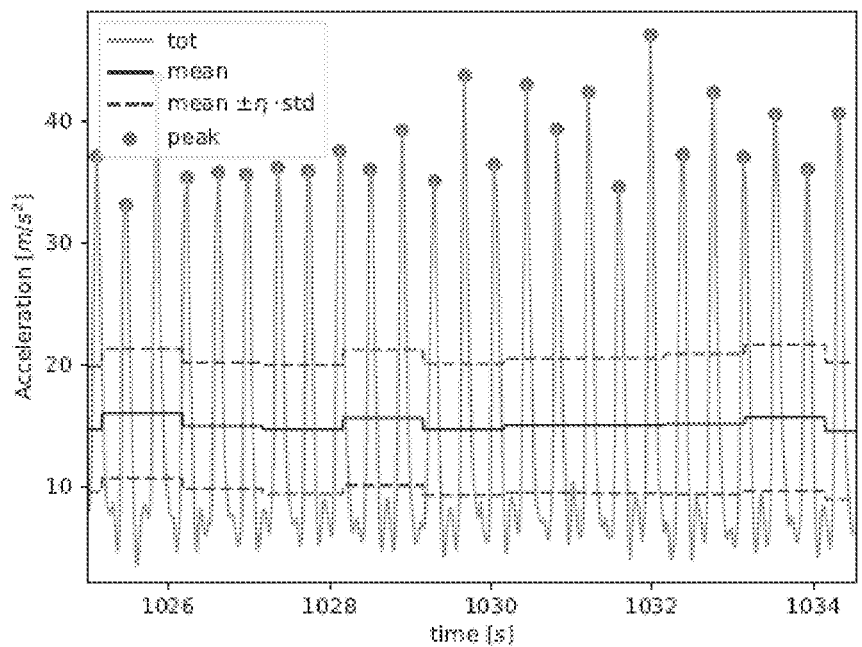
FIG. 2 illustrates a time-acceleration-diagram.

In FIG. 2 a time-acceleration-diagram is illustrated. Acceleration data of the second part of the person 2 as illustrated in FIG. 1, which second part is cyclically moving relative to the first part of the person 2, is recorded over a plurality of cycles using an accelerometer or inertial sensor attached to the second part of the person 2. A characteristic position can be determined based on the acceleration data in subsequent cycles. For each cycle the characteristic position may be, for example, the position of the second part of the person 2, where a maximum acceleration value, i.e. a peak, is measured by means of an accelerometer or inertial sensor. When integrating the acceleration data over the full cycles, the dynamic acceleration, i.e. the motion of the second part in relation to the first part of the person 2, integrates to zero and the tilting of the accelerometer 13 or inertial sensor relative to a horizontal plane can be determined. An external magnetic field can further be measured using a magnetometer in order to determine an orientation of the cyclically moving part relative to the external magnetic field. The geomagnetic orientation of the second part of the person 2 can be determined using the magnetometer attached to the second part of the person 2, for instance.

Another geomagnetic orientation of the second part of the person can be determined in the characteristic position after changing the direction of the first part of the person from a first direction 3 to a second direction 4, and thus the second direction 4 of movement of the first part of the person 2 can be determined based on the deviation between the geomagnetic first orientation and the geomagnetic second orientation of the second part of the person 2.

Figure 3:
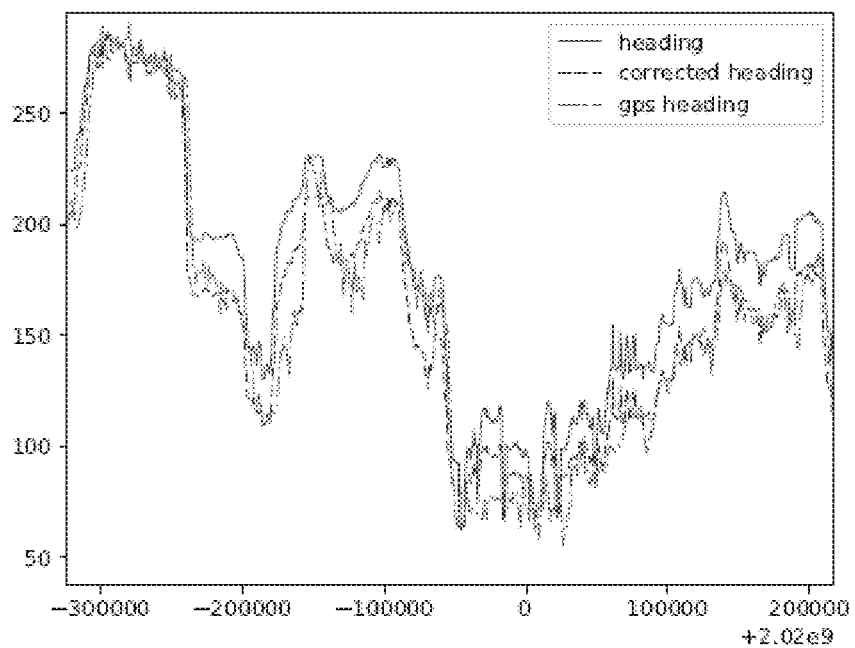
FIG. 3 illustrates a time-direction of movement-diagram.

In FIG. 3 a time-direction of movement-diagram is illustrated. The direction of movement of a runner is shown over time using different methods for determining a direction of movement of an object. The direction of movement is computed based on a method using a GPS positioning system known in the art (marked as "gps heading"), a method for determining the direction of movement of an object in accordance with at least one embodiment of the present invention (marked as "heading") as well as a method for determining the direction of movement of an object in accordance with at least one embodiment of the present invention, wherein certain errors have been corrected (marked as "corrected heading").

On top of the constant offset caused by the misalignment of the lower arm of a runner compared to the direction of movement of the runner, there are other error sources such as misalignment of the magnetometer and accelerometer axes, calibration offsets and integration errors. The combined effect of all these errors is that the difference between true and estimated error is heading dependent. This can be modelled, for example, as $$\theta_{est.} - \theta_{true} = \cos(\theta_{est.} + \alpha) \cdot \beta + \gamma.$$

These parameters can be calibrated when reference directions are available.

It can be seen that the deviation of the direction of movement determined with the method for determining the direction of movement of an object in accordance with at least one embodiment of the present invention, wherein certain errors have been corrected, from the GPS based direction of movement appears to be very small.

Thus, the method for determining the direction of movement of an object in accordance with at least one embodiment of the present invention provides sufficient precision for determining the direction of movement of an object. In particular, after calibration of a system in accordance with at least some embodiments of the invention, the system can be e.g. used in shadow areas as further described in connection with FIGS. 7-10.

Figure 4:
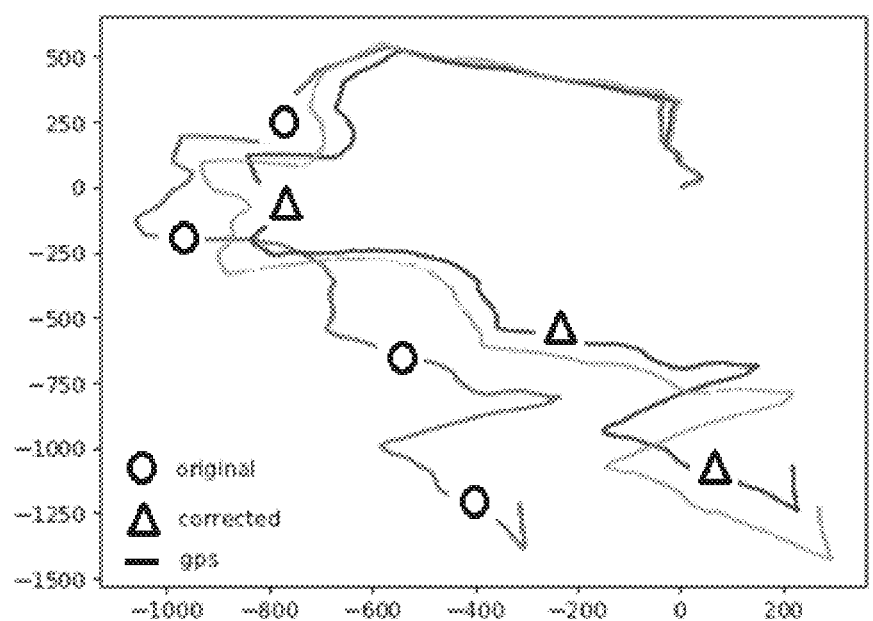
FIG. 4 illustrates a diagram with geometric paths tracked using different methods.

In FIG. 4 a diagram with geometric paths tracked using different methods is illustrated. The geometric path is computed based on a method using a GPS positioning system known in the art (marked as "gps"), a method for determining the direction of movement of an object in accordance with at least one embodiment of the present invention (marked as "original") as well as a method for determining the direction of movement of an object in accordance with at least one embodiment of the present invention, wherein correction of errors as described above in connection with FIG. 3 has taken place (marked as "corrected").

It is possible to track the position of an object by means of the provided compass-system in the coordinate system the as described compass forms. Such a coordinate system is, for example, shown in FIG. 4. A track formed in such a first coordinate system can be aligned with a second coordinate system, for example a geographical coordinate system, and thus a track can be shown in connection with a map. One can even afterwards align the track to a geographical track by calibrating the coordinate system the as described compass has formed.

Thus, the method for determining the direction of movement of an object in accordance with at least one embodiment of the present invention provides sufficient precision for determining the geometric path of an object and/or determining the position of the object. In particular, after calibration of a system in accordance with at least some embodiments of the invention, the system can be e.g. used in shadow areas as further described in connection with FIGS. 7-10.

Figure 5:
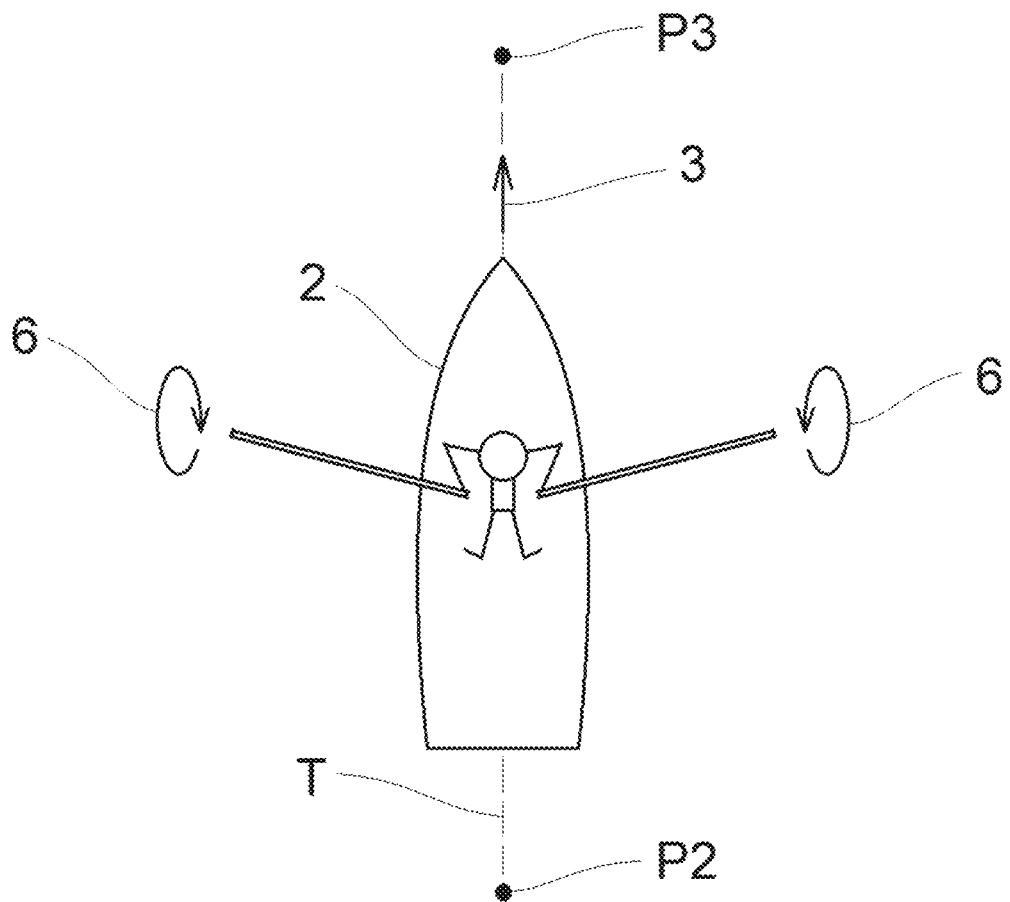
FIG. 5 illustrates another schematic view of an example of determination of a direction of movement of an object in accordance with at least some embodiments of the present invention.

In FIG. 5 another schematic view of an example of determination of a direction of movement of an object in accordance with at least some embodiments of the present invention is illustrated. When a person is rowing a rowing boat 2, the arms of the person move cyclically in relation to the body of the person. On the other side, also the blades of the oars move cyclically in relation to the hull of the rowing boat 2. Consequently, a system in accordance with at least some embodiments of the invention can be either attached to an arm of the person or be attached to or integrated with the blade of an oar. In the first case, a direction of movement of the person can be determined. In the latter case, a direction of movement of the rowing boat 2 can be determined. In other words, the term object in this document has to be understood as a person, an animal or any other three dimensional body.

The direction of movement can be determined by determining a cyclical motion of a cyclically moving part of the object 2 by recording acceleration data of said cyclically moving part over a plurality of cycles using an accelerometer 13 or inertial sensor attached to said cyclically moving part, integrating said acceleration data over at least one cycle of movement to determine a tilting of the cyclically moving part of the object 2 relative to a horizontal plane, measuring an external magnetic field of said cyclically moving part of the object 2 using a magnetometer 12 to determine an orientation of said cyclically moving part of the object 2 relative to the external magnetic field, and determining the direction of movement of the object 2 based on the tilting and the orientation of the cyclically moving part of the object 2.

The direction 3 of movement remains constant as long as the orientation of said cyclically moving part of the object 2 remains constant or substantially constant. Changes in the orientation indicate that either the cyclic motion has changed or that the direction of movement has changed. Changes in the cyclic motion may be, for example, detected by changes in the tilting.

It is possible to track the position of an object by means of the provided compass-system in the coordinate system the as described compass forms. A reference system can be used to either calibrate the calculated direction if the cyclical movement happens in some angle relative to the direction of movement of the object or to calibrate the direction if a local magnetic field is not pointing to the same direction as the reference system, for example, because of a magnetic declination. Of course, the reference system can also be used to calibrate the calculated direction if the cyclical movement happens in some angle relative to the direction of movement of the object and if a local magnetic field is not pointing to the same direction as the reference system.

The position of the object can be tracked in a coordinate system based on the orientation only. However, in case that the coordinate system should be aligned with a geographical coordinate system, the direction of movement of the object 2 is determined based on a previously determined direction 3 of said object 2 and the orientation of the cyclically moving part of the object 2. The previously determined direction 3 may be, for example, determined using an external positioning system 10 such as a GPS system.

Figure 6:
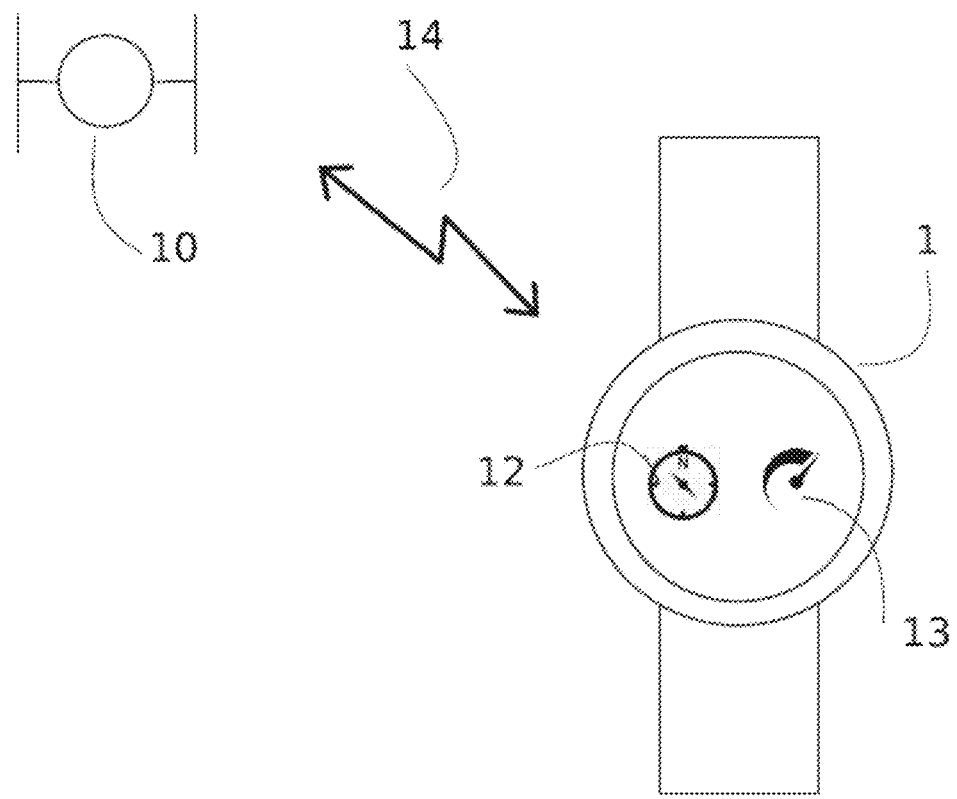
FIG. 6 illustrates a satellite system and a system in accordance with at least some embodiments of the present invention.

In FIG. 6 a schematic view of a satellite system and a system in accordance with at least some embodiments of the present invention is illustrated. A schematic view of a satellite 10 is shown, which may be a GPS satellite, for example. A system 1 is according to the invention equipped both with a magnetometer 12 and acceleration sensor(s) 13. The system 1 may be, for example, the system described in connection with FIG. 1.

A primary position indication of the system 1 is determined based on signals 14 received from the external positioning system 10. From these signals 14 also a first direction of movement of the person can be determined.

The geomagnetic orientation of the system 1 can be calculated based on the accelerometer sensor 13 signals by integrating measured acceleration data over a selected period of time to determine a tilting of said cyclically moving part of the object 2 relative to a horizontal plane and by measuring an external magnetic field of the cyclically moving part in a characteristic position to determine an orientation of said cyclically moving part relative to the external magnetic field. If the movement is rhythmic or cyclic, which it almost always is when a person is carrying the device, any further direction of the person may be obtained from the geomagnetic orientation of the system 1.

Velocity data may then be computed, for example based on the same or different accelerometer sensor 13 signals or any other speed sensor, wheel sensor, tachometer, impeller or pitot tube, and a secondary position indication of the system may be obtained based on a known previous position, direction data, velocity data, and a timing function. The secondary position indication may then be used instead of the primary position indication to determine the position of the system 1 if the quality or availability of the satellite signal falls below a predetermined threshold value.

Figure 7:
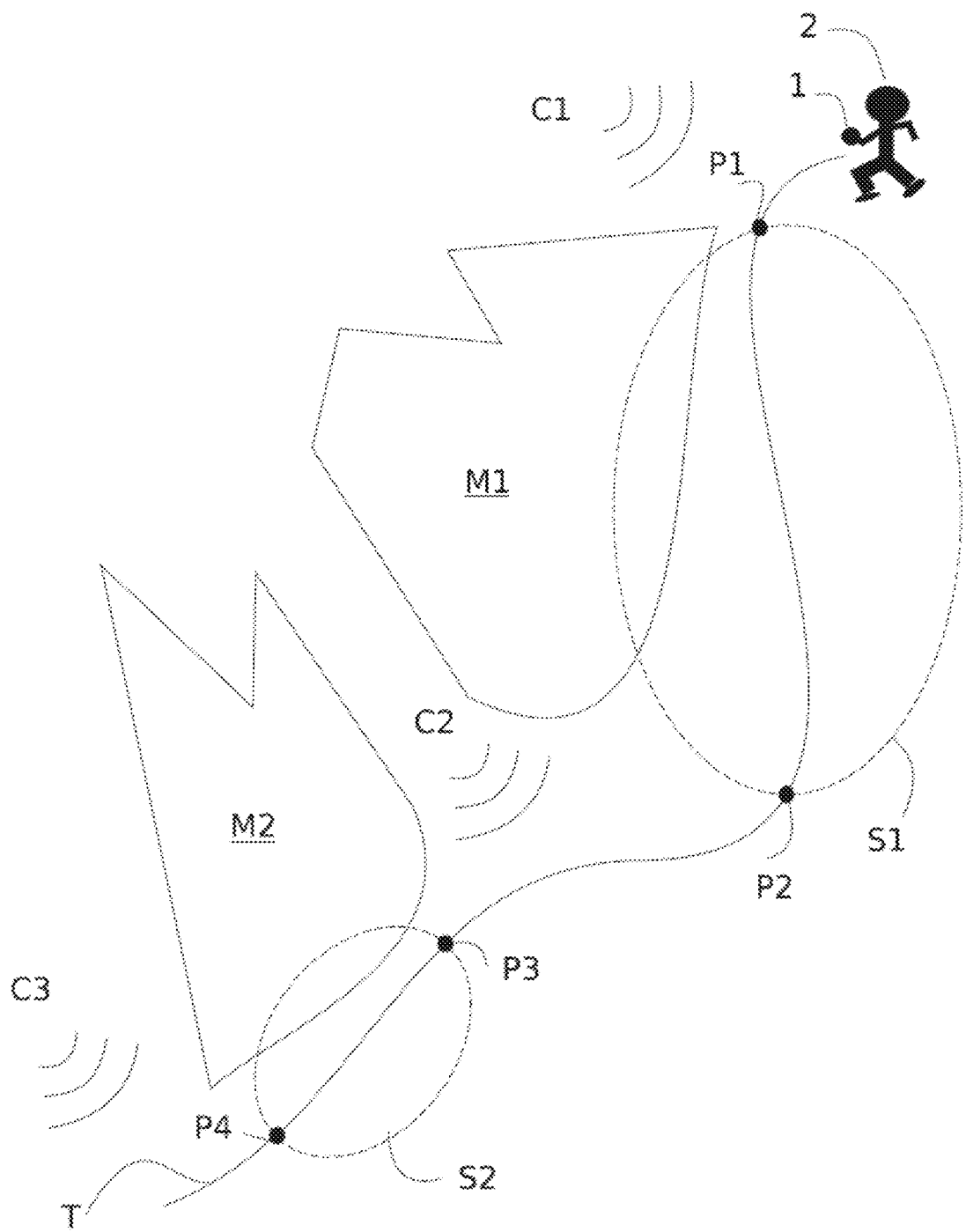
FIG. 7 illustrates a schematic view of an example of outdoor position determination.

In FIG. 7 a schematic view of an example of outdoor position determination is illustrated. A person 2 carrying a system 1 in accordance with certain embodiments of the present invention is about to run or walk along a track T in a mountain area M1, M2. Because of the mountains M1 and M2, the satellite positioning signals have shadow areas S1 and S2 along the track T, where the satellite signals are weak or non-existing. Occasionally along the track T, satellite signal coverage is provided as indicated by radiation patterns C1, C2, C3.

At point P1, the system 1 loses contact with the satellite navigation system as it enters shadow area S1. S1 is then the last known "good" position, i.e. a primary position indication, based on the satellite navigation system. The direction and velocity of the user 2 in the shadow area S iis determined by the processing unit in the system by computing a primary position indication based on signals C1 from the satellite system to determine the position of the user at point P1.

Between points P1 and P2, the processing unit of system 1 records movement data of the user using sensor signals from the accelerometer(s) in the system, and calculates the direction of movement of the user 2 based on the sensor signals as described, for example, in connection with FIG. 1. The processing unit records direction data of the user 2 in a memory unit in order to determine the current direction of the user 2. It also computes the velocity of the user 2 in each direction. The direction and velocity data is stored in the memory unit, in order to track and store secondary position indications of the user along the track T computed as a distance from the last known position at P1. The system 1 may then offer the second position of the user 2 at point P2, based on the secondary position indication at that point. Between point P2 and P3, satellite coverage C2 is again provided, and the position of the user 2 becomes updated with a new primary position indication at point P2 based on signals C2 from the satellite system. When the user 2 enters the shadow area S2 at point P3, the same procedure commences as in shadow area S1. At point P4, a primary position indication based on signals C3 from the satellite system is again available.

For a runner running cross-country also the vertical z direction of the runner, i.e. the change in altitude, may be recorded in addition to any direction in a horizontal plane. Recording of the vertical z direction may be performed by using altitude data calculated from air pressure data measured by means of an air pressure sensor, for instance. Mapping this information onto a topographic map vs. time gives information of the ground speed and position of the runner.

Figure 8:
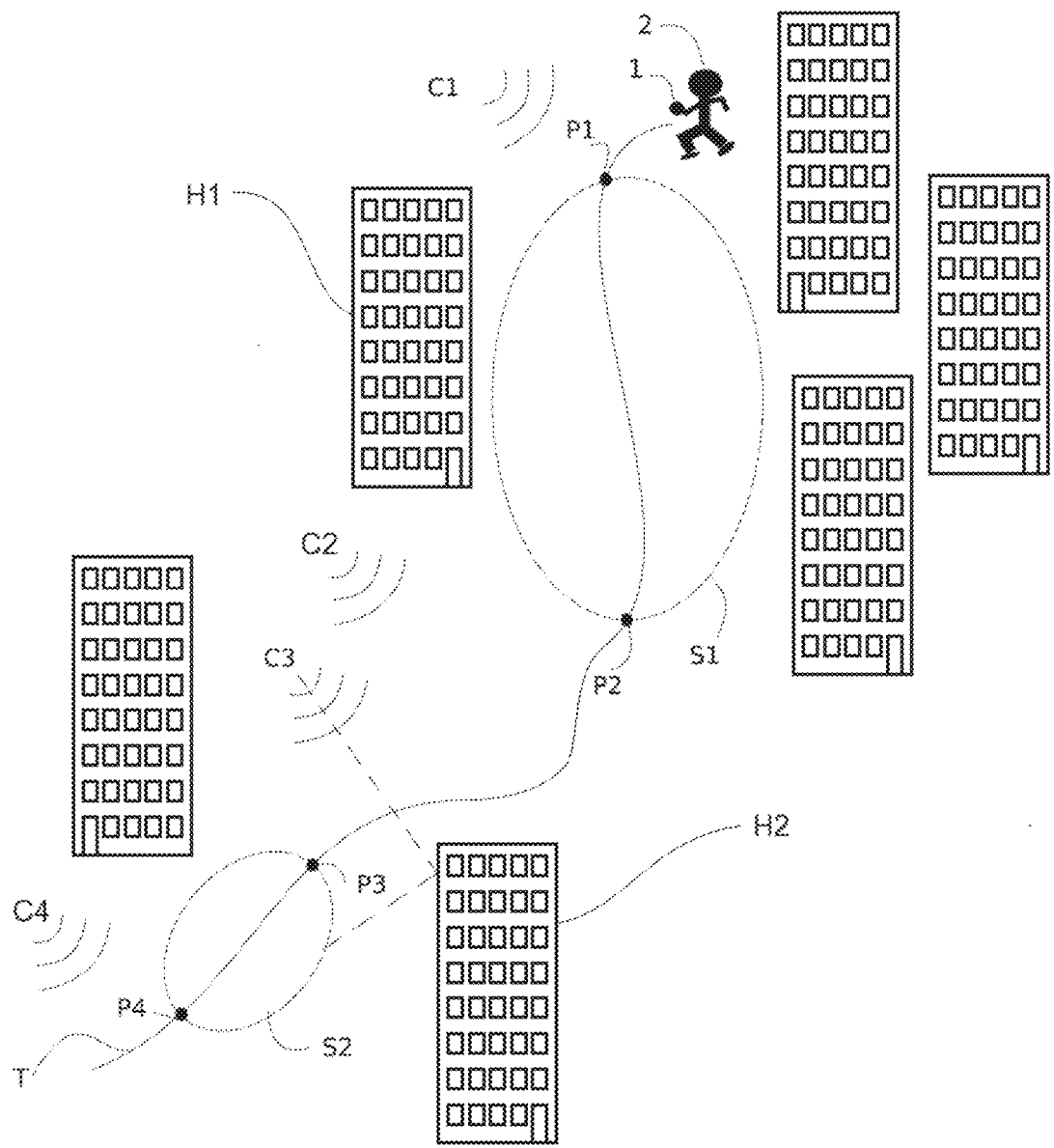
FIG. 8 illustrates a schematic view of another example of outdoor position determination.

In FIG. 8 a schematic view of another example of outdoor position determination is illustrated. A person 2 carrying a system 1 in accordance with certain embodiments of the present invention is about to run or walk along a track T in an urban area between different buildings. Because of the buildings, the satellite positioning signals have shadow areas S1 and S2 along the track, where the satellite signals are weak, non-existing, or ambiguous. Occasionally along the track T, satellite signal coverage is provided as indicated by radiation patterns C1, C2, C3, C4.

At point P1, the system 1 loses contact with the satellite navigation system as it enters shadow area S1. S1 is then the last known "good" position, i.e. a primary position indication, based on the satellite navigation system. The direction and velocity of the user 2 in the shadow area S1 is determined by the processing unit in the system by computing a primary position indication based on signals C1 from the satellite system to determine the position of the user at point P1.

Between points P1 and P2, the processing unit of system 1 records movement data of the user using sensor signals from the accelerometer(s) in the system, and calculates the direction of movement of the user based on the sensor signals as described, for example, in connection with FIG. 1. The processing unit records direction data of the user in a memory unit in order to determine the current direction of the user 2. It also computes the velocity of the user in each direction and determines the time the person has moved in any direction. The direction and velocity data is stored in the memory unit, in order to track and store secondary position indications of the user 2 along the track T computed as a distance from the last known position at P1. The system 1 may then offer the second position of the user 2 at point P2, based on the secondary position indication at that point. Between point P2 and P3, satellite coverage C2 is again provided, and the position of the user becomes updated with a new primary position indication at point P2 based on signals C2 from the satellite system.

When the user 2 enters the shadow area S2 at point P3, the satellite signal C3 is reflected by the building H2, and thus the position of the person is ambiguous. The processing unit of system 1 records movement data of the user using sensor signals from the accelerometer(s) in the system, and calculates the direction of movement of the user 2 based on the sensor signals as described, for example, in connection with FIG. 1. The processing unit records direction data of the user 2 in a memory unit in order to determine the current direction of the user 2. It also computes the velocity of the user in each direction and determines the time the person has moved in any direction. The direction and velocity data is stored in the memory unit, in order to track and store secondary position indications of the user 2 along the track T computed as a distance from the last known position at P3. At point P4, a primary position indication based on signals C4 from the satellite system is again available.

A primary position indication may be determined within specific time intervals, for example every 30 seconds or every minute, from the external positioning system. The quality of the signal of the external positioning system may also be determined within a specific time interval. The time interval for determining a primary position indication and the time interval for determining the quality of the signal of the external positioning system may be different or identical. The quality of the signal of the external positioning system may be determined based on the signal strength and/or availability, for instance. If the signal strength is below a specific threshold value or a signal cannot be received at all from the external positioning system, the secondary position indication of the user 2 may be calculated. Calculation of the secondary position indication may also take place permanently. The tracked secondary position indication may be also displayed on a display of the system 1, for example in connection with a map.

Figure 9:
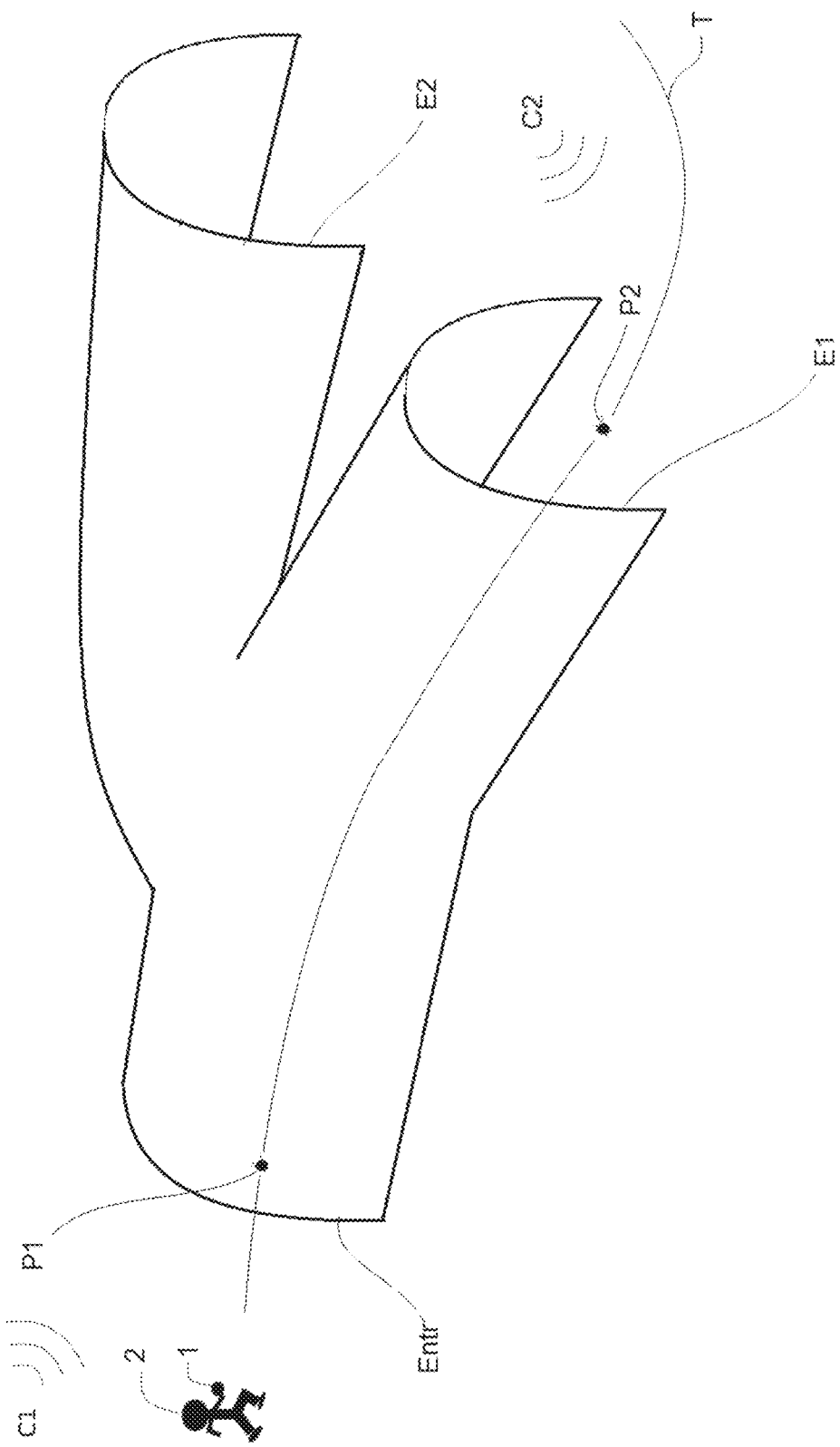
FIG. 9 illustrates a schematic view of an example of indoor position determination.

In FIG. 9 a schematic view of an example of indoor position determination is illustrated. A person 2 carrying a system 1 in accordance with certain embodiments of the present invention is about to run or walk along a track T through a tunnel or tunnel system. The tunnel has an entrance Entr and two separate exits E1, E2. Occasionally along the track T, satellite signal coverage is provided as indicated by radiation patterns C1, C2. Because of the tunnel, the satellite positioning signals are lost between the entrance Entr of the tunnel at point P1 and the exit E1 of the tunnel at point P2.

The direction and velocity of the user 2 in the tunnel is determined by the processing unit in the system by computing a primary position indication based on signals C1 from the satellite system to determine the position of the user at point P1.

Between points P1 and P2, the processing unit of system 21 records movement data of the user using sensor signals from the accelerometer(s) in the system, and calculates the direction of movement of the user based on the sensor signals as described, for example, in connection with FIG. 1. The processing unit records direction data of the user 2 in a memory unit in order to determine the current direction of the user 2. It also computes the velocity of the user 2 in each direction and determines the time the person has moved in any direction. The direction and velocity data is stored in the memory unit, in order to track and store secondary position indications of the user 2 along the track T computed as a distance from the last known position at P1. The system 1 may then offer the second position of the user 2 at point P2, based on the secondary position indication at that point. At point P2, satellite coverage C2 is again provided, and the position of the user becomes updated with a new primary position indication at point P2 based on signals C2 from the satellite system. Thus, it is possible to calculate and/or monitor the position of the person within a tunnel or tunnel system. In particular, it is possible to calculate and/or monitor in which part of the tunnel or tunnel system the person 2 is located or has been located.

As there is no satellite signal available along the track T between points P1 and P2, the secondary position indication of the person 2 may be determined based on said primary position indication, said direction data, and said velocity data within specific time intervals, for instance. A time interval may be, for example, 1 second, 5 seconds, or 10 seconds. In other words, as long as there is no satellite signal available between points P1 and P2, calculating and/or monitoring of the secondary position indication may take place every second, for instance. Accordingly, secondary position indication data, velocity data, and direction data may be stored every second in the memory of a system in accordance with certain embodiments of the present invention. According to certain embodiments of the present invention, secondary position indication data, velocity data, and direction data may be in addition or instead transmitted via a wireless connection to a server infrastructure or any other computing device. Of course, the data may be also read out at a later stage.

At least one of the secondary position indication data, velocity data, and direction data may be visualized on a display of the system in accordance with some embodiments of the present invention. In particular, the secondary position indication data may be shown on a map on the display of the system. The secondary position indication data may be visualized in real time or at a later stage. According to certain embodiments, the tracked secondary position indication data may be shown on a map on a display of another device in real time or at a later stage. According to certain other embodiments, the tracked secondary position indication data may be shown on a map, which is accessible via the internet, in real time or at a later stage. Further, data derivable from at least one of the secondary position indication data, velocity data, and direction data may be visualized on the display of the system in accordance with some embodiments of the present invention, on another device, or in the internet. Of course, also data obtained or derivable from the primary indication data may be visualized on the display of the system in accordance with some embodiments of the present invention, on another device, or in the internet.

Further, the two external positioning signals at points P1 and P2 can be used for calibrating at least one of the direction of movement, the calculation of the secondary position indication and the sensors of the system 1. In general, any two or more external positioning signals can be used for calibration. Calibration may take place permanently, i.e. also when the external positioning signal is available, or within specific time intervals, for instance. A permanent calibration of the calculation of the secondary position indication between two different external positioning signals is beneficial, because a well calibrated system is provided in case that an external positioning signal is not available or the quality of the signal is not sufficient. The calibration may be personalized. For example, a person may wear a system 1 in accordance with some embodiments of the present invention in the form of a wrist watch. Different persons may move their arms differently when walking or running, and thus different accelerations may be measured by the acceleration sensors, even when the persons walk or run with identical velocity. Each system 1 may be calibrated differently due to such different accelerations taking place. In other words, calibration of the system 1 may be personalized, in particular by permanently calibrating the calculation of the secondary position indication.

In the tunnel example of FIG. 9, the calculated secondary position indication should be at point P2 identical with the new primary position indication received from the external positioning system at point P2. Any deviation between the secondary position indication and the new primary position indication can be used to calibrate multiple parameters. Independent parameters may be, for example, speed and direction. A mathematical optimization algorithm may be used for calibration of the multiple parameters. For example, the least-squares method or the simplex method may be used. The mathematical procedures can be used for finding the best-fitting curve to a given set of points by minimizing the sum of the squares of offsets of the points from the curve, for instance. When applying such a so called least-square fitting, the sum of the squares of the offsets is used instead of the absolute values. The least-squares method finds its optimum when the sum of squared offsets is a minimum. Thus, effects of different sources of error can be balanced in order to provide a best fit for the position of the person.

Figure 10:
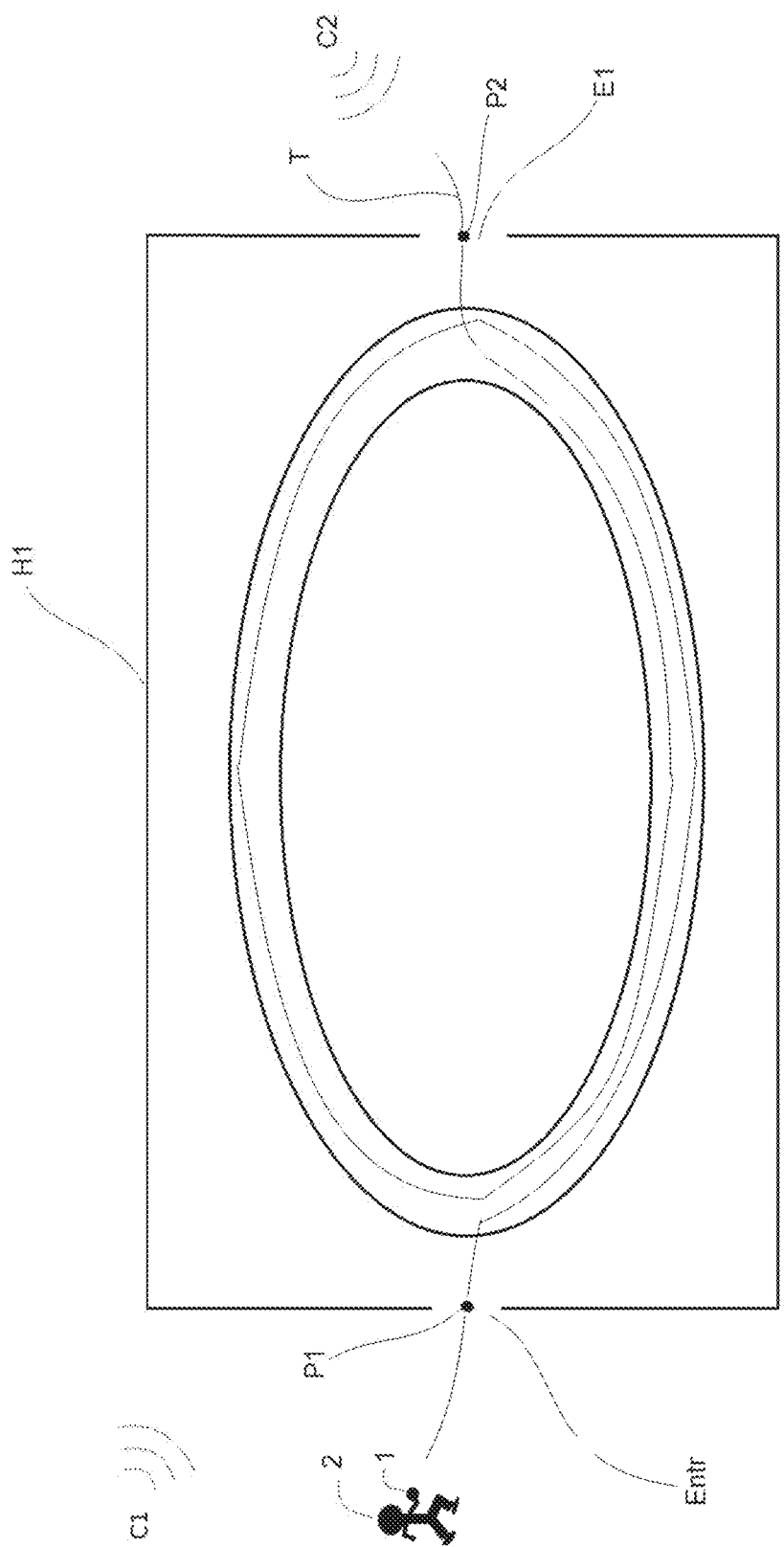
FIG. 10 illustrates a schematic view of another example of position determination.

In FIG. 10 a schematic view of another example of indoor position determination is illustrated. A person 2 carrying a system 1 in accordance with certain embodiments of the present invention is about to run or walk along a track T within a building H1, for example a sports stadium. The building H1 has an entrance Entr and an exit E1. The satellite positioning signals are lost between the entrance Entr of the building H1 at point P1 and the exit E1 of the building H1 at point P2 along the track T.

The position, direction, and velocity of the user 2 within the building H1 is determined by the processing unit in the system by computing a primary position indication based on signals C1 from the satellite system to determine the position of the user at point P1 when entering the building H1.

Between points P1 and P2, the processing unit of system 21 records movement data of the user using sensor signals from the accelerometer(s) in the system, and calculates the direction of movement of the user 2 based on the sensor signals as described, for example, in connection with FIG. 1. The processing unit records direction data of the user 2 in a memory unit in order to determine the current direction of the user 2. It also computes the velocity of the user 2 in each direction and determines the time the person 2 has moved in any direction. The direction and velocity data is stored in the memory unit, in order to track and store secondary position indications of the user 2 along the track T.

Within the building H1 the person 2 may run or walk a specific distance along a 400 m lane, for instance. The position, velocity, and direction of the user 2 as well as the covered distance can be computed and/or monitored within the building H1 by means of the system 1 in accordance with some embodiments of the present invention. In particular, also changes in velocity and direction of the user can be calculated and/or monitored. In other words, the system 1 is configured to calculate any position between the points P1 and P2. The calculation particularly also includes changes in direction of a moving person 2. In the example of FIG. 10, the person 2 moves along half of a round of the 400 m lane towards point P2, then moves along half of a round of the 400 m lane towards point P1, and subsequently moves again along half of a round of the 400 m lane towards point P2. Such changes in direction can be calculated by the system using the provided magnetometer data. Thus, any trajectory of the person 2 between points P1 and P2, where an external positioning signal is not available or the quality is not sufficient, can be calculated and/or monitored by the system 1.

When leaving the building H1 via the exit E1 at point P2, the system 1 may then offer the second position of the user 2 at point P2, based on the secondary position indication at that point. At point P2, satellite coverage C2 is again provided, and the position of the user becomes updated with a new primary position indication at point P2 based on signals C2 from the satellite system. Thus, it is possible to calculate and/or monitor the position, velocity, and direction of the person 2 within the building H1 between points P1 and P2.

Figure 11:
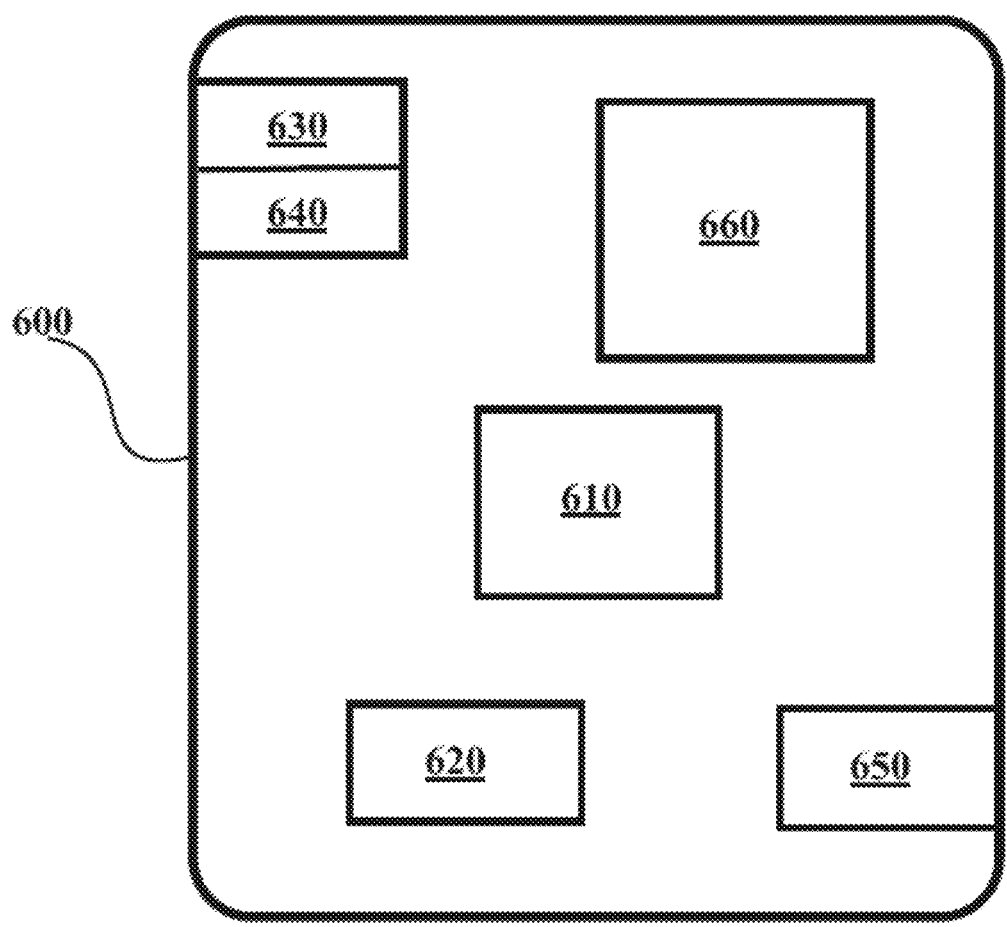
FIG. 11 illustrates an example of a system in accordance with at least some embodiments of the present invention.

In FIG. 11 an example of a system in accordance with at least some embodiments of the present invention is illustrated. Illustrated is system 600, which may comprise, for example, a readout system or an integrated system comprising readout and analytics functions. Comprised in system 600 is processor 610, which may comprise, for example, a single- or multi-core processor wherein a single-core processor comprises one processing core and a multi-core processor comprises more than one processing core. Processor 610 may comprise more than one processor. A processing core may comprise, for example, a Cortex-A8 processing core manufactured by ARM Holdings or a Steamroller processing core produced by Advanced Micro Devices Corporation. Processor 610 may comprise at least one Qualcomm Snapdragon and/or Intel Atom processor. Processor 610 may comprise at least one application-specific integrated circuit, ASIC. Processor 610 may comprise at least one field-programmable gate array, FPGA. Processor 610 may be means for performing method steps in system 600. Processor 610 may be configured, at least in part by computer instructions, to perform actions.

The system 600 may comprise memory 620. Memory 620 may comprise random-access memory and/or permanent memory. Memory 620 may comprise at least one RAM chip. Memory 620 may comprise solid-state, magnetic, optical and/or holographic memory, for example. Memory 620 may be at least in part accessible to processor 610. Memory 620 may be at least in part comprised in processor 610. Memory 620 may be means for storing information. Memory 620 may comprise computer instructions that processor 610 is configured to execute. When computer instructions configured to cause processor 610 to perform certain actions are stored in memory 620, and system 600 overall is configured to run under the direction of processor 610 using computer instructions from memory 620, processor 610 and/or its at least one processing core may be considered to be configured to perform said certain actions. Memory 620 may be at least in part external to system 600 but accessible to system 600.

System 600 may comprise a transmitter 630. System 600 may comprise a receiver 640. Transmitter 630 and receiver 640 may be configured to transmit and receive, respectively, information in accordance with at least one communication standard. Transmitter 630 may comprise more than one transmitter. Receiver 640 may comprise more than one receiver. Transmitter 630 and/or receiver 640 may be configured to operate in accordance with global system for mobile communication, GSM, wideband code division multiple access, WCDMA, 5G, long term evolution, LTE, IS-95, wireless local area network, WLAN, Ethernet and/or worldwide interoperability for microwave access, WiMAX, standards, for example. Receiver 640 is configured to receive signals from an external positioning system, for example a GPS satellite signal. System 600 may comprise a single receiver 640 or a plurality of different receivers 640.

System 600 may comprise a readout circuitry 650. System 600 may comprise user interface, UI, 660. UI 660 may comprise at least one of a display, a keyboard, a button, a touchscreen, a vibrator arranged to signal to a user by causing system 600 to vibrate, a speaker and a microphone. A user may be able to operate system 600 via UI 660, for example to start and stop monitoring of position data.

Processor 610 may be furnished with a transmitter arranged to output information from processor 610, via electrical leads internal to system 600, to other systems comprised in system 600. Such a transmitter may comprise a serial bus transmitter arranged to, for example, output information via at least one electrical lead to memory 620 for storage therein. Alternatively to a serial bus, the transmitter may comprise a parallel bus transmitter. Likewise processor 610 may comprise a receiver arranged to receive information in processor 610, via electrical leads internal to system 600, from other systems comprised in system 600. Such a receiver may comprise a serial bus receiver arranged to, for example, receive information via at least one electrical lead from receiver 640 for processing in processor 610. Alternatively to a serial bus, the receiver may comprise a parallel bus receiver.

Processor 610, memory 620, transmitter 630, receiver 640, readout circuitry 650 and/or UI 660 may be interconnected by electrical leads internal to system 600 in a multitude of different ways. For example, each of the aforementioned systems may be separately connected to a master bus internal to system 600, to allow for the systems to exchange information. However, as the skilled person will appreciate, this is only one example and depending on the embodiment various ways of interconnecting at least two of the aforementioned systems may be selected without departing from the scope of the present invention.

According to a certain embodiment, the system 600 further includes a x-, y-, z-accelerometer and a x-, y-, z-magnetometer. An air pressure sensor may be an additional optional feature. I.e., the system 600 comprises devices for measuring acceleration in three dimensions, for measuring direction in three dimensions as well as for measuring air pressure. A direction, a velocity, and a position of a user can be derived from the measured data in connection with the primary position indication. The system is further configured to record the time an object has moved in any direction by a timing function.

According to another certain embodiment, the system 600 further includes a x-, y-, z-accelerometer, a x-, y-, z-gyroscope, and a x-, y-, z-magnetometer as well as an air pressure sensor. The gyroscope can be added to the system in order to mitigate the effect of magnetic disturbances and situations when the cyclic motion is disturbed, for example when a person is waiving the hands. If the orientation is known at the beginning, integrating gyroscope data can theoretically tell the orientation at any later point in time. Because of the sensor errors, gyroscope measurements need to be fused with other sensor measurements. The gyroscope adds extra error sources to the system. Gyroscope errors can be estimated using the behaviour of the data. Integration of the gyroscope signal over selected subsequent cycles should be zero, assuming that the direction of movement has not changed. Thus, the direction of movement can also be determined by using gyroscope data in addition to accelerometer and magnetometer data. Furthermore, the gyroscope enables definition of a cycle in a different way. If a cycle is estimated from peaks in the accelerometer signal, there is some latency, since the peak is not accepted instantly. However, zero crossings of the gyroscope signal can be used to estimate the cycle to give the detection without latency. This means that there is no need to buffer gyroscope data for integration. In the case of a wrist device, it is convenient to calculate the cycle from zero crossings of the function $$f = \omega_g - \omega_z,$$

where $w_i$ are gyroscope measurements and assuming that the x-direction is pointing to the direction of movement.

The system 600 may be, for example, a smartphone or a tablet computer according to some embodiments. According to other embodiments, the system may be a wristop computer. The above mentioned devices may be all comprised in a single apparatus or separated from each other in different devices of a system. For example, an accelerometer, a gyroscope, a magnetometer, an air pressure sensor, and a receiver configured to receive a signal from an external positioning system may be comprised by a wristop computer. According to another certain embodiment, an accelerometer, a magnetometer, and an air pressure sensor may be comprised by a wristop computer. The receiver configured to receive a signal from an external positioning system and the processor 610 may be comprised by a separate computing device. The wristop computer and the computing device are then configured to transmit and receive data via a personal area network. In other words, acceleration data, direction data, and pressure data may be measured by the wristop computer and transmitted to the computing device. The external positioning signal may be additionally received by the computing device. The velocity of said moving object in said direction based on the accelerometer sensor signals may then be computed by the computing device and the secondary position indication of said object may be determined by the computing device. Finally, the tracked secondary positioning signal may then be displayed by the computing device.

System 600 may comprise a further device not illustrated in FIG. 11. In some embodiments, system 600 lacks at least one device described above.

It is to be understood that the embodiments of the invention disclosed are not limited to the particular structures, process steps, or materials disclosed herein, but are extended to equivalents thereof as would be recognized by those ordinarily skilled in the relevant arts. It should also be understood that terminology employed herein is used for the purpose of describing particular embodiments only and is not intended to be limiting.

Reference throughout this specification to one embodiment or an embodiment means that a particular feature, structure, or characteristic described in connection with the embodiment is included in at least one embodiment of the present invention. Thus, appearances of the phrases "in one embodiment" or "in an embodiment" in various places throughout this specification are not necessarily all referring to the same embodiment. Where reference is made to a numerical value using a term such as, for example, about or substantially, the exact numerical value is also disclosed.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. In addition, various embodiments and example of the present invention may be referred to herein along with alternatives for the various components thereof. It is understood that such embodiments, examples, and alternatives are not to be construed as de facto equivalents of one another, but are to be considered as separate and autonomous representations of the present invention.

Furthermore, the described features, structures, or characteristics may be combined in any suitable manner in one or more embodiments. In the following description, numerous specific details are provided, such as examples of lengths, widths, shapes, etc., to provide a thorough understanding of embodiments of the invention. One skilled in the relevant art will recognize, however, that the invention can be practiced without one or more of the specific details, or with other methods, components, materials, etc. In other instances, well-known structures, materials, or operations are not shown or described in detail to avoid obscuring aspects of the invention.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

The verbs "to comprise" and "to include" are used in this document as open limitations that neither exclude nor require the existence of also un-recited features. The features recited in depending claims are mutually freely combinable unless otherwise explicitly stated. Furthermore, it is to be understood that the use of "a" or "an", that is, a singular form, throughout this document does not exclude a plurality.

INDUSTRIAL APPLICABILITY

At least some embodiments of the present invention find industrial application in determining a direction of movement of an object.

ACRONYMS LIST

GPS Global Positioning System
GSM global system for mobile communication
LTE long term evolution
UI user interface
WCDMA wideband code division multiple access
WiMAX worldwide interoperability for microwave access
WLAN wireless local area network

REFERENCE SIGNS LIST 1 system
2 object
3 first direction
4 second direction
5 third direction
6 cyclical motion
10 satellite
12 magnetometer
13 accelerometer
14 signal
600 system
610 processor
620 memory
630 transmitter
640 receiver
650 readout circuitry
660 user interface
C1 satellite signal
C2 satellite signal
C3 satellite signal
C4 satellite signal
E1 first exit
E2 second exit
Entr entrance
H1 building
H2 building
M1 mountain
M2 mountain
P1 first point
P2 second point
P3 third point
P4 fourth point
T track

CITATION LIST

Patent Literature

GB 2497153

The invention claimed is:

1. A method for determining and tracking an indoor position of an object comprising
    using a primary position indication, based on signals received from an external positioning system of at least two different positions of said object to calibrate tracking of a secondary position indication, which is an indoor position, and wherein after calibrated, the tracking of the secondary position comprises:
    recording acceleration data of a second part of the object, which second part is cyclically moving relative to the first part of the object, over a plurality of cycles using a sensor attached to the second part of the object,
    integrating said acceleration data over at least one cycle of movement to determine a tilting of said cyclically moving part of the object relative to a horizontal plane,
    determining a characteristic position of the cyclically moving second part of the object in subsequent cycles,
    measuring a geomagnetic first orientation of the second part of the object in said characteristic position,
    determining the second direction of movement of the first part of the object by measuring a geomagnetic second orientation of the second part of the object in said characteristic position, and wherein the determination is based on the tilting and the deviation between the geomagnetic first orientation and the geomagnetic second orientation of the second part of the object,
    computing a velocity of the object in any direction based on the acceleration data, and
    determining the secondary position indication of said object based on said direction data and said velocity data, wherein the secondary position indication is used to determine the indoor position of said object,
    wherein at least one of:
        a first angle between the geomagnetic first orientation of the second part of the object and the first direction of the first part of the object; or
        a second angle between the geomagnetic first orientation and the geomagnetic second orientation of the second part of the object is determined.

2. The method according to claim 1, comprising continuously tracking and computing at least one of the direction and the velocity of the moving object, and said secondary position indication.

3. The method according to claim 1, wherein a third angle between the geomagnetic second orientation of the second part of the object and the second direction of the first part of the object is identical with the first angle.

4. The method according to claim 1, wherein a position of the first part of the object is determined with the use of at least one of: an accelerometer or an inertial sensor to determine the acceleration data, a magnetometer to determine the geomagnetic orientation of the second part of the object, and a timing function used to record the time the object has moved in any direction.

5. The method according to claim 1, wherein the time the object has moved in any direction is recorded by a timing function.

6. The method according to claim 1, wherein the calibration is personalized such that different accelerations are measured by acceleration sensors even when the velocities are identical.

7. The method according to claim 1, wherein air pressure is measured by means of an air pressure sensor and an altitude of said object is determined based on the air pressure.

8. The method according to claim 1, wherein the secondary position indication of the moving object is displayed on a display of a system, transmitted from the system to another device, or shown on a map which is available via internet.

9. The method according to claim 1, wherein the primary position indication is determined based on GPS signals.

10. The method according to claim 1, wherein the secondary position indication is determined in real time or at a later stage.

11. The method according to claim 1, wherein the characteristic position of each cycle is at a maximum or minimum acceleration value.

12. The method according to claim 1, wherein a track formed in a first coordinate system is aligned with a second coordinate system.

13. A system for determining and tracking indoor position of an object, the system comprising:

a receiver for receiving signals from an external positioning system,
at least one of an accelerometer and an inertial sensor,
a magnetometer,
at least one memory unit, and
a processing unit comprising at least one processing core,
at least one memory including computer program code, the at least one memory and the computer program code being configured to, with the at least one processing core, cause the system at least to:
use a primary position indication, based on signals received from an external positioning system of at least two different positions of said object to calibrate tracking of a secondary position indication, which is an indoor position,
record acceleration data of a second part of the object, which second part is cyclically moving relative to the first part of the object, over a plurality of cycles using an accelerometer or inertial sensor attached to the second part of the object,
integrate said acceleration data over at least one cycle of movement to determine the tilting of said cyclically moving part of the object relative to the horizontal plane,
determine a characteristic position in subsequent cycles,
measure a geomagnetic first orientation of the second part of the object in a characteristic position of subsequent cycles using a magnetometer,
measure a geomagnetic second orientation of the second part of the object in the characteristic position of each cycle using the magnetometer,
determine a second direction of the first part of the moving object based on the tilting and a deviation between the geomagnetic first orientation and the geomagnetic second orientation of the second part of the object,
compute a velocity of the object in any direction based on the acceleration data, and
determine the secondary position indication of said object based on said direction data and said velocity data, wherein the secondary position indication is used to determine the indoor position of said object,
wherein the system is configured to determine at least one of a first angle between the geomagnetic first orientation of the second part of the object and the first direction of the first part of the object or a second angle between the geomagnetic first orientation and the geomagnetic second orientation of the second part of the object.

14. The system according to claim 13, wherein the processing unit is configured to continuously compute and store at least one of the direction, the velocity, and the secondary position indication of the moving object.

15. The system according to claim 13, wherein the system is configured to determine the primary position indication of the object based on GPS signals between two separate points of time.

16. The system according to claim 13, wherein the system is configured to track at least one of the first direction, the second direction, an acceleration, the velocity and a position of the first part of the moving object.

17. The system according to claim 13, wherein the system is configured to determine a position of the object with the use of at least one of: the accelerometer or inertial sensor to determine the acceleration data, the magnetometer to determine the first orientation and the second orientation of the second part of the object, and a timing function used to record the time the object has moved in any direction.

18. The system according to claim 13, wherein the system is configured to record the time the object has moved in any direction by a timing function.

19. The system according to claim 13, wherein the system is configured to personalize the calibration such that different accelerations are measured by acceleration sensors even when the velocities are identical.

20. The system according to claim 13, wherein the system further comprises an air pressure sensor.

21. The system according to claim 13, wherein the system is configured to display a position of the moving object on a display of the system, to transmit the position of the moving object from the system to another device, or to show the position of the moving object on a map which is available via internet.

22. The system according to claim 13, wherein the system is configured to determine the position in real time or at a later stage.

23. The system according to claim 13, wherein the system further comprises a gyroscope.

24. The system according to claim 13, wherein the system is configured to align a track formed in a first coordinate system with a second coordinate system.

25. The system according to claim 13, wherein the system is one of a mobile device, a wristop computer, a mobile telephone and a portable device.

26. A non-transitory computer readable medium having stored thereon a set of computer readable instructions that, when executed by at least one processor, cause an apparatus to at least to:
use a primary position indication, based on signals received from an external positioning system, of at least two different positions of said object, configured to calibrate track of a secondary position indication, which is an indoor position,
record acceleration data of a second part of the object, which second part is cyclically moving relative to the first part of the object, over a plurality of cycles using a sensor attached to the second part of the object,
integrate said acceleration data over at least one cycle of movement to determine the tilting of said cyclically moving part of the object relative to the horizontal plane,
determine a characteristic position in subsequent cycles,
measure a geomagnetic first orientation of the second part of the object in a characteristic position of subsequent cycles,
measure a geomagnetic second orientation of the second part of the object in the characteristic position of each cycle,
determine a second direction of the first part of the moving object based on the tilting and a deviation between the geomagnetic first orientation and the geomagnetic second orientation of the second part of the object,
compute velocity of the object any direction based on the acceleration data, and
determine the secondary position indication of said object based on said direction data and said velocity data, wherein the secondary position indication is used to determine the indoor position,
and determine at least one of:
a first angle between the geomagnetic first orientation of the second part of the object and the first direction of the first part of the object; or a second angle between the geomagnetic first orientation and the geomagnetic second orientation of the second part of the object.

\* \* \* \* \*